United States Patent
Murase (10) Patent No.: US 9,562,875 B2
(45) Date of Patent: Feb. 7, 2017

(54) MEASURING APPARATUS, DETECTION METHOD, ELECTROCHEMICAL SENSOR AND MEASURING SYSTEM

(71) Applicant: ARKRAY, Inc., Kyoto (JP)

(72) Inventor: Yosuke Murase, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 0 days.

(21) Appl. No.: 14/873,419

(22) Filed: Oct. 2, 2015

(65) Prior Publication Data
US 2016/0097733 A1    Apr. 7, 2016

(30) Foreign Application Priority Data

Oct. 3, 2014  (JP) .................................. 2014-204638
Sep. 11, 2015 (JP) .................................. 2015-179321

(51) Int. Cl.
*G01N 27/327*  (2006.01)
*A61B 5/145*   (2006.01)

(52) U.S. Cl.
CPC ....... *G01N 27/3271* (2013.01); *A61B 5/14532* (2013.01); *G01N 27/3274* (2013.01)

(58) Field of Classification Search
CPC ................................................ A61B 5/14532
See application file for complete search history.

(56) References Cited

U.S. PATENT DOCUMENTS

| 2009/0030641 | A1  | 1/2009 | Fjield et al. |
| 2010/0169035 | A1* | 7/2010 | Liang ................. A61B 5/14532 702/65 |
| 2012/0199496 | A1  | 8/2012 | Sekimoto |

FOREIGN PATENT DOCUMENTS

| JP | 2012-176229 A     | 9/2012  |
| WO | 2007/131036 A1    | 11/2007 |
| WO | WO 2007/131036 A1 * | 11/2007 |

OTHER PUBLICATIONS

Extended European Search Report issued in corresponding European Patent Application No. 15188125.7 dated Feb. 23, 2016.

* cited by examiner

*Primary Examiner* — J. Christopher Ball
(74) *Attorney, Agent, or Firm* — Morgan, Lewis & Bockius LLP (57) ABSTRACT

A measuring apparatus for measuring a substrate concentration by using a sensor including an enzyme reagent layer includes a state detecting unit that applies a first voltage and a second voltage different from the first voltage to the sensor to detect a state of the enzyme reagent layer based on a difference between a first response current value obtained under application of the first voltage and a second response current value obtained under application of the second voltage.

12 Claims, 10 Drawing Sheets

MEASURING APPARATUS, DETECTION METHOD, ELECTROCHEMICAL SENSOR AND MEASURING SYSTEM

This application claims the benefit of Japanese Patent Application No. 2014-204638 filed on Oct. 3, 2014 and No. 2015-179321 filed on Sep. 11, 2015 in the Japanese Patent Office, the disclosure of which is herein incorporated in its entirety by reference.

FIELD

The disclosure relates to a measuring apparatus, a detection method, an electrochemical sensor and a measuring system.

BACKGROUND

As a subcutaneous indwelling type glucose sensor, one in which an enzyme reagent layer is provided on a working electrode and the enzyme reagent layer (or the whole sensor in general) is covered with an outer layer film for restricting diffusion of a substrate in the enzyme reagent layer is known.

The outer layer film of such a glucose sensor is degraded during use of the sensor (over time elapsing after subcutaneous indwelling). When the outer layer film is degraded, an error occurs in a measurement result of a glucose concentration, and therefore, a technique for detecting that the outer layer film has been degraded (a defect has been caused in the outer layer film) has been developed.

Specifically, a technique in which a voltage for obtaining a response derived from a substrate is continuously applied to a sensor, a time T at which change of a response current value caused immediately after the voltage application becomes smaller or larger than a change threshold value is measured, and it is determined that a defect has been caused in an outer layer film if the time T is smaller than a time threshold value (see, for example, Patent Document 1) has been developed.

[Patent document 1] Japanese Patent Laid-Open No. 2012-176229

According to the aforementioned technique, although it may be detected that the outer layer film of the sensor has been degraded, it is impossible to detect that the enzyme reagent layer of the sensor has been degraded. Besides, the enzyme reagent layer of the sensor may be degraded prior to the outer layer film in some cases. Therefore, there is a demand for a technique in which a state (a normal state, a degraded state or the like) of an enzyme reagent layer of a sensor including an outer layer film and the enzyme reagent layer, such as the aforementioned glucose sensor, may be detected.

Besides, in some of glucose sensors not of the subcutaneous indwelling type, the diffusion is restricted without providing an outer layer film (for example, as in a self monitoring blood glucose sensor for measuring a Cottrell current), but a technique in which degradation of an enzyme reagent layer of such a sensor has also not been developed at present.

Accordingly, an object of an embodiment of the present invention is to provide a technique in which a state of an enzyme reagent layer of a sensor including an outer layer film and a sensor not including an outer layer film may be detected.

SUMMARY

The present inventor made earnest studies, for solving the aforementioned problems, on a detection method for a state of an enzyme reagent layer of a sensor including the enzyme reagent layer. As a result, it has been found that a state of an enzyme reagent layer may be detected, in a sensor including the enzyme reagent layer, based on a difference between two response current values obtained by applying two different voltages no matter whether or not an outer layer film is provided (which will be described in detail later).

The embodiment is accomplished based on the aforementioned finding through further examination, and for solving the aforementioned problems, a measuring apparatus for measuring a substrate concentration by using a sensor including an enzyme reagent layer includes: state detecting means that applies a first voltage and a second voltage different from the first voltage to the sensor to detect a state of the enzyme reagent layer based on a difference between a first response current value obtained under application of the first voltage and a second response current value obtained under application of the second voltage.

The difference between the first response current value and the second response current value obtained under application of the aforementioned voltages is varied depending on a state of the enzyme reagent layer. Accordingly, when the measuring apparatus including the state detecting means having the above-described function is used, the state of the enzyme reagent layer provided in the sensor may be detected.

The measuring apparatus may be provided as an apparatus in which the sensor is a sensor whose response current value increases in accordance with increase in an applied voltage substantially at a first increase rate when the applied voltage is in a low voltage range, and increases at a second increase rate smaller than the first increase rate when the applied voltage is in a high voltage range higher than the low voltage range, and at least one of the first voltage and the second voltage is a voltage within the high voltage range.

As the state detecting means of the measuring apparatus, means that "detects that the enzyme reagent layer has been in a degraded state when the difference obtained by applying, as the second voltage, a voltage higher than a general measurement voltage corresponding to the first voltage is equal to or larger than a threshold value" or means that "detects that the enzyme reagent layer has been in a precursory state of a degraded state when the difference obtained by applying, as the second voltage, a voltage lower than a general measurement voltage corresponding to the first voltage is equal to or larger than a threshold value" may be employed. Incidentally, when the latter means is employed as the state detecting means, it may be detected that the enzyme reagent layer has started to be degraded (that time when degradation of the enzyme reagent layer starts to harmfully affect a measurement current value has approached) before a measurement current value is affected by the degradation of the enzyme reagent layer and an inaccurate substrate concentration is obtained.

Besides, a detection method for detecting a state of an enzyme reagent layer provided in a sensor of the includes: a step of applying a first voltage to the sensor to measure a response current value of the sensor in response to the first voltage; a step of applying a second voltage different from the first voltage to the sensor to measure a response current value of the sensor in response to the second voltage; and a step of detecting the state of the enzyme reagent layer based on a difference between the measured two response current values. The difference between the two response current values measured by this detection method also indicates a state of the enzyme reagent layer. Accordingly, a state of an enzyme reagent layer provided in a sensor may be detected also by the detection method.

Besides, an electrochemical sensor is an electrochemical sensor connected to the above-described measuring apparatus, and a measuring system: a measuring apparatus that applies a voltage to a sensor connected thereto to measure a substrate concentration based on a response current value obtained under application of the voltage; and an electrochemical sensor that is connected to the measuring apparatus, and includes an enzyme reagent layer, and a plurality of electrodes to which a first voltage and a second voltage are applied in order that the measuring apparatus detects a state of the enzyme reagent layer based on a difference between a first response current value obtained under application of the first voltage and a second response current value obtained under application of the second voltage different from the first voltage.

According to the embodiment, a state of an enzyme reagent layer of a sensor may be detected no matter whether or not an outer layer film is provided.

DESCRIPTION OF EMBODIMENTS

An embodiment of the present invention will now be described with reference to the accompanying drawings.

It is noted that a measuring apparatus 1 according to one embodiment of the present invention described below is an apparatus for detecting a state of a sensor 4 of a subcutaneous indwelling type in which an enzyme reagent layer is provided on a working electrode and the enzyme reagent layer is covered with an outer layer film for restricting diffusion of a substrate. The present invention may be, however, applied to not only a sensor of the subcutaneous indwelling type in which the diffusion is restricted by the outer layer film but also a sensor not of the subcutaneous indwelling type in which the diffusion is restricted without providing an outer layer film. Besides, the present invention may be applied also to a sensor used for performing any of continuous measurement, repeated measurement and single measurement.

Figure 1:
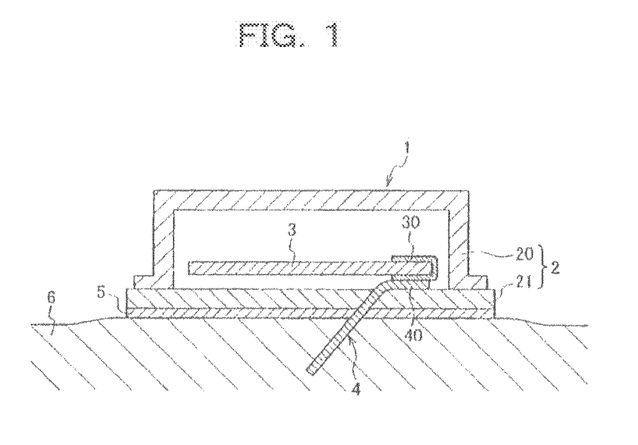
FIG. 1 is an explanatory diagram illustrating a structure and a use form of a measuring apparatus according to one embodiment.

FIG. 1 illustrates the structure and the use form of the measuring apparatus 1 according to one embodiment of the present invention.

The measuring apparatus 1 of the present embodiment is a CGM (Continuous Glucose Monitoring) apparatus attached to a skin 6 of a belly, a shoulder or the like of a human body for continuously measuring a concentration of glucose in a blood or a subcutaneous interstitial fluid.

The sensor 4 having an end portion 40 placed in the measuring apparatus 1 is an exchangeable glucose sensor of the subcutaneous indwelling type. As described above, an enzyme reagent layer is provided on a working electrode of the sensor 4, and the enzyme reagent layer of the sensor 4 is covered with an outer layer film for restricting the diffusion of a substrate. As this sensor 4, any one of various sensors different in the specific structure may be used.

Figure 2:
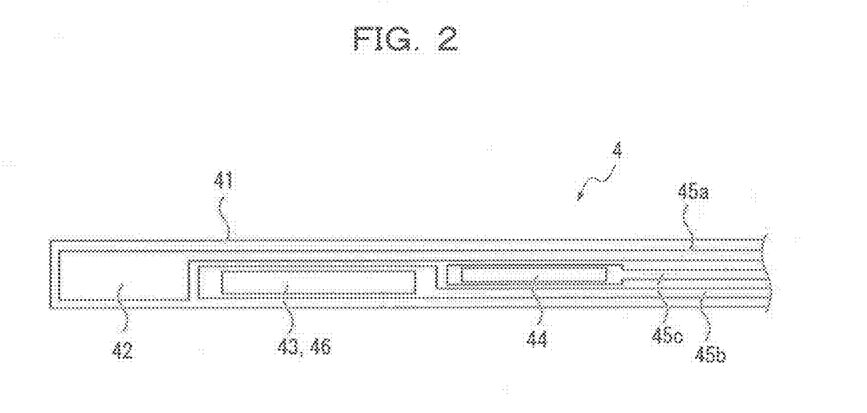
FIG. 2 is an explanatory diagram illustrating an example of an electrode structure of a sensor usable in the measuring apparatus of the embodiment.

For example, the sensor 4 may be a sensor in which a counter electrode 42, the working electrode 43 and a reference electrode 44 are arranged in a tip portion of a narrow and long base member 41 along the lengthwise direction of the base member 41 as schematically illustrated in FIG. 2. It is noted that the counter electrode 42 of the sensor 4 illustrated in FIG. 2 corresponds to a tip portion of a metal pattern 45a formed on the base member 41. The reference electrode 44 corresponds to a layer of, for example, Ag/AgCl provided in a tip portion of a metal pattern 45c formed on the base member 41. The working electrode 43 corresponds to, for example, a carbon layer provided in a tip portion of a metal pattern 45b formed on the base member 41. The enzyme reagent layer 46 is provided on this working electrode 43.

Alternatively, the sensor 4 may be a sensor in which a counter electrode 42, a working electrode 43 and a reference electrode 44 are arranged along the widthwise direction of a base member 41, or a sensor having merely two electrodes (that is, a working electrode 43 and a reference electrode 44 or a counter electrode 42).

As the constituent material of the base member 41 of the sensor 4, a material having appropriate insulating property and flexibility and having no harmful effect on the human body, for example, a thermoplastic resin, such as PET (polyethylene terephthalate), PP (polypropylene) or PE (polyethylene), may be used. Alternatively, as the constituent material of the base member 41, a thermosetting resin such as a polyimide resin or an epoxy resin may be used.

The enzyme reagent layer 46 provided on the working electrode 43 is a layer on which a glucose oxidation/reduction enzyme is immobilized. As the glucose oxidation/reduction enzyme, GOD (glucose oxidase) or GDH (glucose dehydrogenase) may be used. Besides, as an immobilization method for the glucose oxidation/reduction enzyme, any of known methods may be employed. Specifically, as the immobilization method for the glucose oxidation/reduction enzyme, a method using a polymer such as a polymerizable gel, polyacrylamide or phosphorus, a method using an MPC polymer obtained by binding a phospholipid polymer with a silane coupling agent, or a method using a protein coating may be employed.

Figure 3:
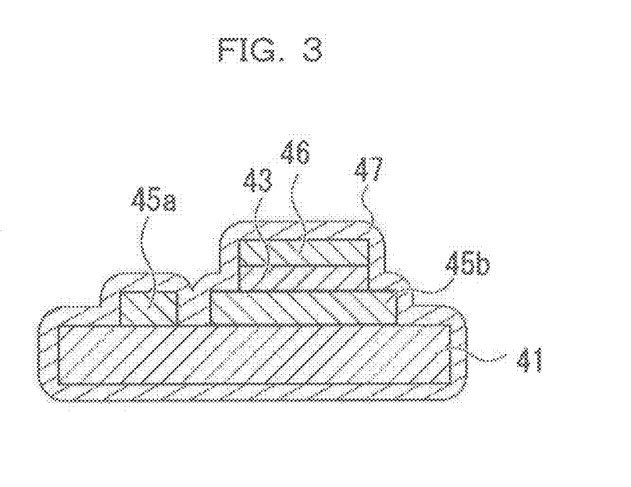
FIG. 3 is an explanatory diagram of an example of a shape of an outer layer film of the sensor.

The outer layer film covering the enzyme reagent layer 46 of the sensor 4 may be a layer of a single substance or a film including a plurality of stacked layers as long as it has a function to restrict the diffusion of a substrate. Besides, the outer layer film may not be one covering the enzyme reagent layer 46 alone. For example, as schematically illustrated in FIG. 3, the outer layer film 47 may be a film in a shape covering the entire sensor 4.

Referring to FIG. 1 again, the measuring apparatus 1 will be described. As illustrated in this drawing, the measuring apparatus 1 includes a housing 2 and a printed circuit 3 housed in the housing 2. The housing 2 is a case, constituted by a base 21 having an opening for inserting the sensor 4 and a cover 20, for protecting the printed circuit 3 and the end portion 40 of the sensor 4. In order to prevent the printed circuit 3 or the end portion 40 of the sensor 4 from being degraded/shorted by water or sweat, a material having low water permeability, such as a metal or a polypropylene resin, for example, is preferably used as the constituent material of the housing 2 (the cover 20 and the base 21).

Figure 4:
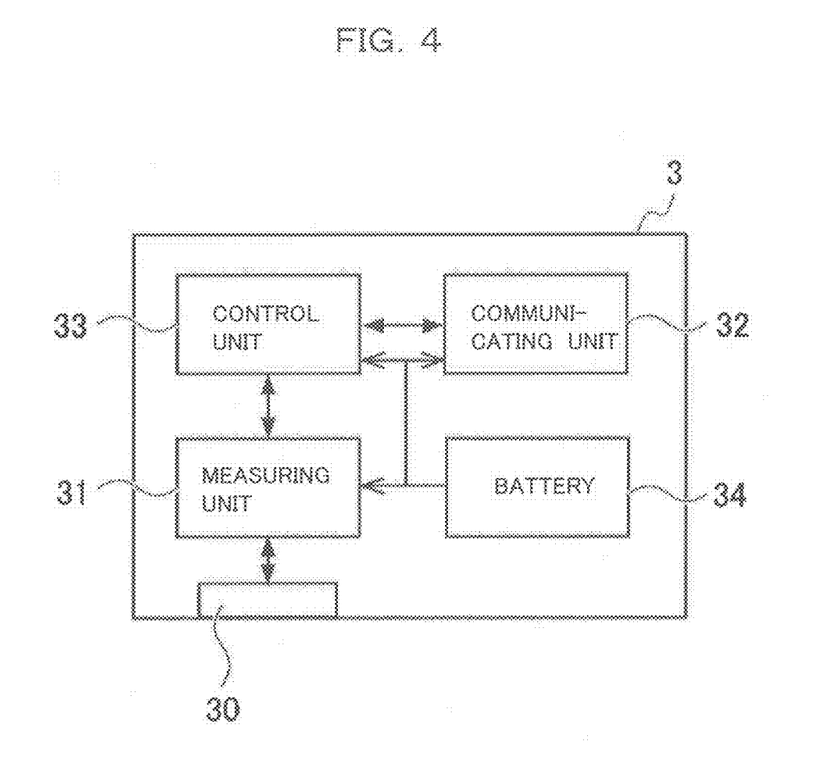
FIG. 4 is a block diagram of a printed circuit included in the measuring apparatus of the embodiment.

The printed circuit 3 is a unit including various types of devices mounted on a printed wiring board. The printed circuit 3 includes, as illustrated in FIG. 4, a connecting unit 30, a measuring unit 31, a communicating unit 32, a control unit 33 and a battery 34 serving as a power source for these units.

The connecting unit 30 is a member for electrically connecting the sensor 4 and the printed circuit 3 to each other.

Specifically, N contact pads electrically connected respectively to the N (which is 3 when the sensor 4 has the structure as illustrated in FIG. 2) electrodes provided at the tip of the sensor 4 are provided in the end portion 40 of the sensor 4. On the other hand, N contact pads electrically connected to the printed circuit 3 are provided in the connecting unit 30. The N contact pads of the connecting unit 30 are provided in positions to be respectively brought into contact with the N contact pads of the end portion 40 when the end portion 40 of the sensor 4 is sandwiched between the connecting unit 30 and the base 21. Besides, the measuring apparatus 1 (see FIG. 1) is an apparatus in which the sensor 4 is attached (respective components are assembled) so that the end portion 40 of the sensor 4 may be sandwiched between the connecting unit 30 and the base 21 with the tip portion of the sensor 4 protruded outside the measuring apparatus 1 through the opening of the base 21, and is an apparatus caused to adhere, for use, to the skin 6 with adhesive force of an adhesive film (a double-coated adhesive tape) 5 adhering to an outer surface of the base 21.

The measuring unit 31 (FIG. 4) of the printed circuit 3 is a circuit that measures a response current value by applying a voltage to the sensor 4 connected to the connecting unit 30 (what is called a potentiostat). The communicating unit 32 is a circuit for communicating (exchanging information) with an external apparatus by wire or wireless. Here, an external apparatus refers to a dedicated apparatus configured to perform various setting processing for the measuring apparatus 1 or processing for recording/displaying measurement results acquired from the measuring apparatus 1, or a computer in which a program for causing a CPU to perform such processing is installed.

The control unit 33 is a unit including a CPU, a ROM, a RAM and the like for controlling the measuring unit 31 and the communicating unit 32.

The control unit 33 operates as follows. Incidentally, the operation of the control unit 33 described below is attained when the CPU included in the control unit 33 executes a program stored in a ROM (for example, a flash ROM) included in the control unit 33.

The control unit 33 applies a prescribed voltage to the sensor 4 by controlling the measuring unit 31 in a measurement cycle, set by a user by using the external apparatus, to measure a response current value of the sensor 4. Besides, the control unit 33 stores therein a glucose concentration calculated based on a measurement result. Furthermore, when the external apparatus is connected, the control unit 33 performs processing for informing the external apparatus of the calculated glucose concentration by using the communicating unit 32.

When the external apparatus demands information (a measurement result of a glucose concentration, measurement date and time, and the like), the control unit 33 transmits demanded information to the external apparatus.

In addition to the aforementioned functions, the control unit 33 has a function to repeat, in a cycle set by the user by using the external apparatus, state detection processing of a type set by the user by using the external apparatus.

The state detection processing that may be executed by the control unit 33 includes first state detection processing, second state detection processing and third state detection processing.

The first state detection processing is processing for detecting (determining) whether the state of the enzyme reagent layer of the sensor 4 is a normal state or a degraded state. The second state detection processing is processing for detecting whether the state of the enzyme reagent layer of the sensor 4 is a normal state or a pre-degraded state. Besides, the third state detection processing is processing for detecting whether the state of the enzyme reagent layer of the sensor 4 is a normal state, a pre-degraded state or a degraded state. Here, a degraded state refers to a state where the enzyme reagent layer is degraded (a state where the sensor 4 does not normally function). Besides, a pre-degraded state refers to a state where the enzyme reagent layer is to be in a degraded state in a prescribed time period (for example, 2 or 3 days) (in other words, a precursory state of a degraded state). A normal state refers to a state that is neither a degraded state nor a pre-degraded state.

Now, contents of the first through third state detection processing will be successively described. Incidentally, a response current value of the sensor 4 in response to a given applied voltage mentioned in the following description refers to a response current value of the sensor 4 obtained by applying the applied voltage. Besides, a difference between measured two response current values refers to "a response current value of the sensor 4 in response to a higher applied voltage−a response current value of the sensor 4 in response to a lower applied voltage".

A first applied voltage refers to a voltage applied to the sensor 4 in general glucose concentration measurement. A second applied voltage refers to an applied voltage predetermined so that it may be higher than the first applied voltage and that an amount of substrate-independent current (an amount of current generated by electrolysis of water and the like) generated under the voltage application may be a voltage of a negligible level. A third applied voltage refers to an applied voltage predetermined to be lower than the first applied voltage. It is noted that appropriate values of the first through third applied voltages are varied depending on the specifications of the sensor 4 (such as an amount of the enzyme used, the immobilization method for the enzyme employed, the materials of the electrodes, and a reaction region). Accordingly, the first through third applied voltages are determined in consideration of the specifications of the sensor 4.

<<First State Detection Processing>>

Figure 5:
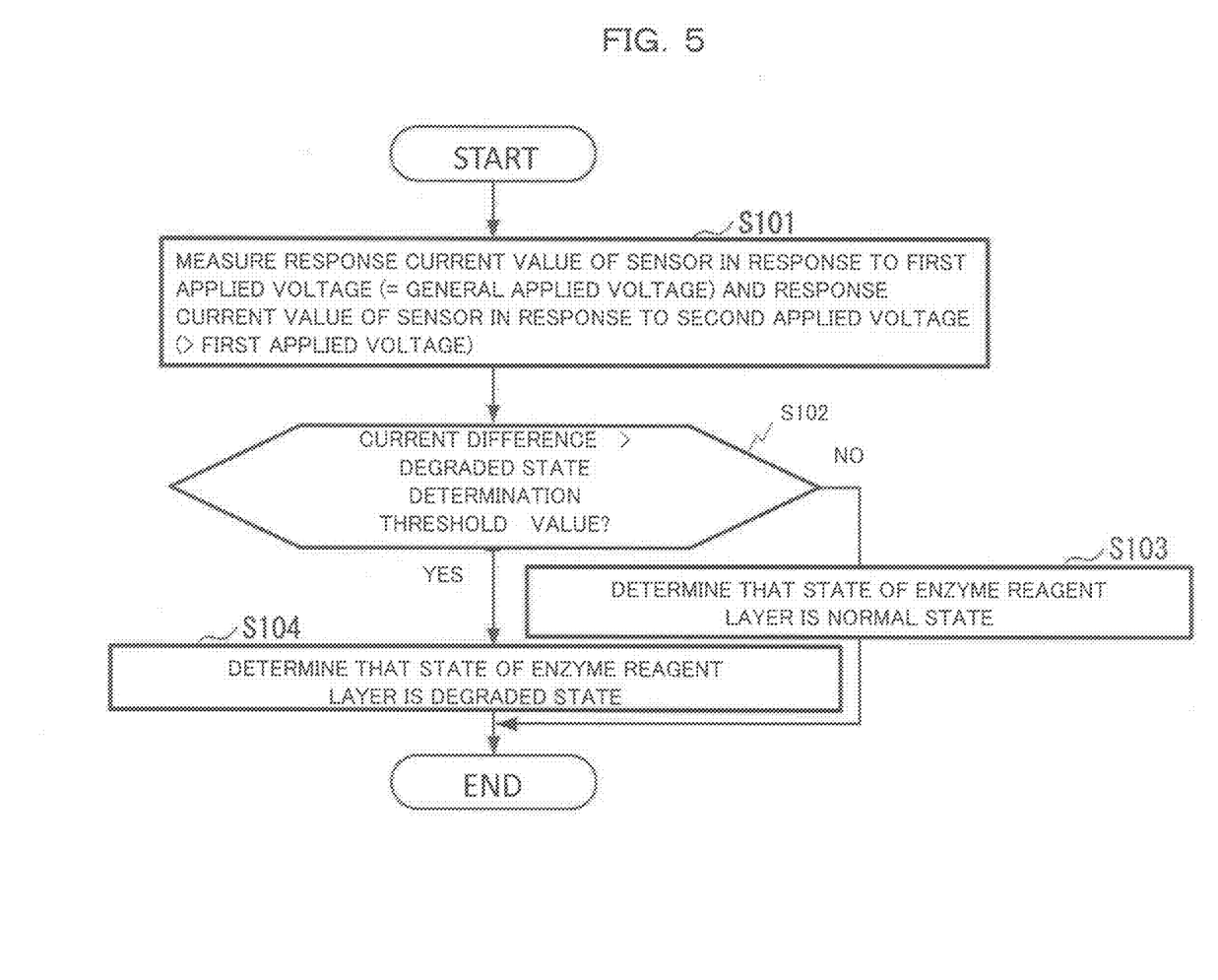
FIG. 5 is a flowchart of first state detection processing that may be executed by a control unit of the printed circuit.

The first state detection processing is processing performed through procedures illustrated in FIG. 5.

Specifically, the control unit 33 having started the first state detection processing in accordance with setting by a user first controls the measuring unit 31 to measure a response current value of the sensor 4 in response to the first applied voltage and a response current value of the sensor 4 in response to the second applied voltage (step S101).

The control unit 33 having completed the processing of step S101 determines whether or not a difference between the measured two response current values is larger than a degraded state determination threshold value (step S102). Here, the degraded state determination threshold value refers to a predetermined value. As the degraded state determination threshold value, a value obtained by adding, to a difference between the two response current values obtained when the enzyme reagent layer is normal, a value several times as large as a measurement error may be employed.

When the difference between the measured two response current values is a value equal to or smaller than the degraded state determination threshold value (step S102; NO), the control unit 33 determines that the state of the enzyme reagent layer of the sensor 4 is a normal state (step S103), and terminates the first state detection processing. Incidentally, the processing performed in step S103 of the first state detection processing of the present embodiment is processing for storing, together with date and time of the determination, that the determination result of the state of the enzyme reagent layer is a normal state. However, no processing may be performed in step S103.

When the difference between the measured two response current values is a value larger than the degraded state determination threshold value (step S102; YES), the control unit 33 determines that the state of the enzyme reagent layer of the sensor 4 is a degraded state (step S104). Then, the control unit 33 performs, in step S104, processing for storing, together with date and time of the determination, that the determination result of the state of the enzyme reagent layer is a degraded state. Thereafter, when the external apparatus is not connected, the control unit 33 terminates the first state detection processing.

On the other hand, when the external apparatus is connected, the control unit 33 transmits, in step S104, information indicating that the determination result of the state of the enzyme reagent layer currently obtained is a degraded state to the external apparatus, and then terminates the first state detection processing. Then, the external apparatus having received the information displays, in a display, a message that the enzyme reagent layer has been degraded. In other words, the external apparatus informs the user of the measuring apparatus 1 that the enzyme reagent layer has been degraded.

<<Second State Detection Processing>>

Figure 6:
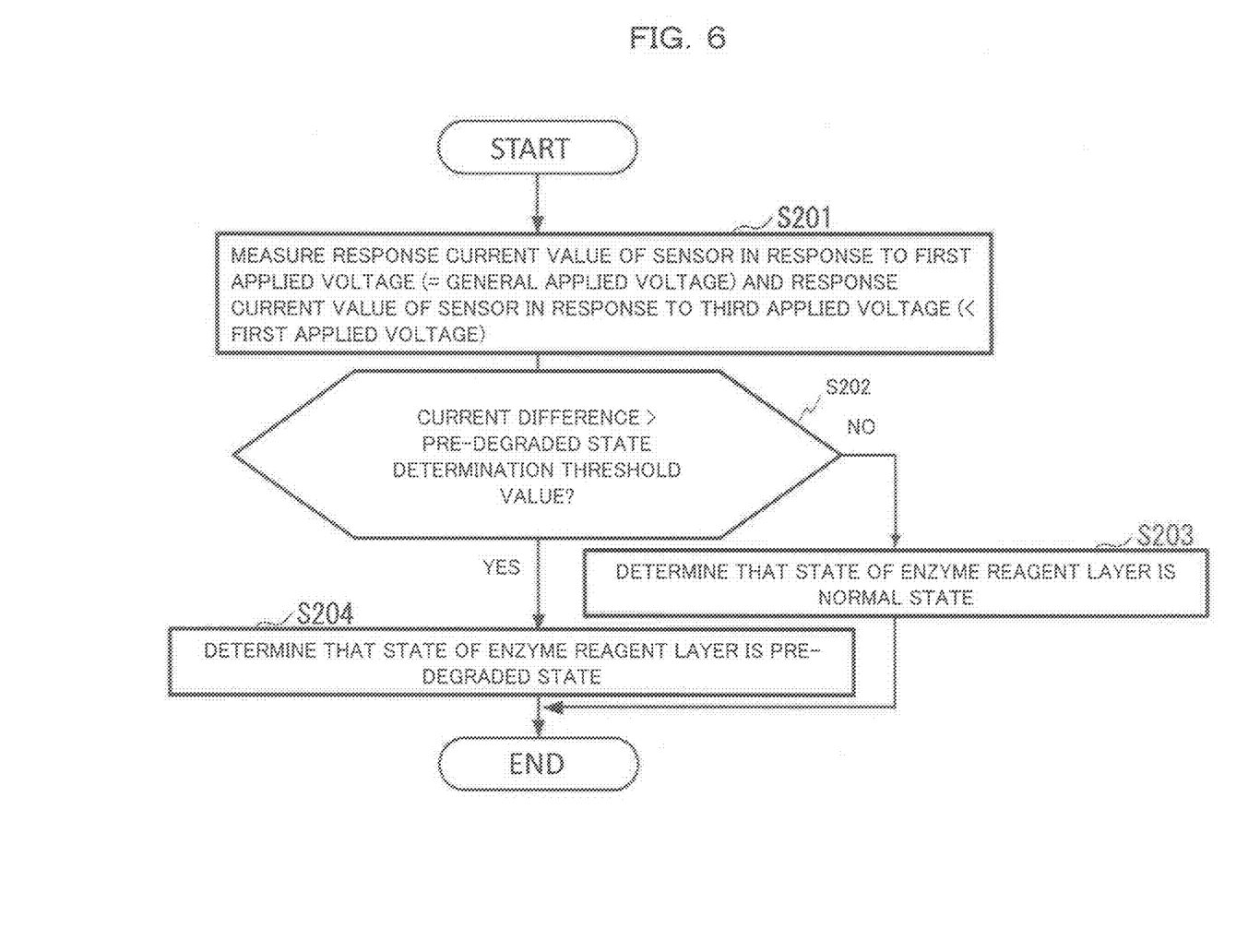
FIG. 6 is a flowchart of second state detection processing that may be executed by the control unit of the printed circuit.

The second state detection processing is processing performed through procedures illustrated in FIG. 6. Specifically, the control unit 33 having started the second state detection processing in accordance with setting by a user first controls the measuring unit 31 to measure a response current value of the sensor 4 in response to the first applied voltage and a response current value of the sensor 4 in response to the third applied voltage (step S201).

Subsequently, the control unit 33 determines whether or not a difference between the measured two response current values (=the response current value of the sensor 4 in response to the first applied voltage–the response current value of the sensor 4 in response to the third applied voltage) is a value larger than a pre-degraded state determination threshold value (step S202). Here, the pre-degraded state determination threshold value is a predetermined value. As the pre-degraded state determination threshold value, similarly to the degraded state determination threshold value described above, a value obtained by adding, to a difference between the two response current values obtained when the enzyme reagent layer is normal, a value several times as large as a measurement error may be employed.

When the difference between the measured two response current values is a value equal to or smaller than the pre-degraded state determination threshold value (step S202; NO), the control unit 33 determines that the state of the enzyme reagent layer of the sensor 4 is a normal state (step S203), and terminates the second state detection processing.

On the other hand, when the difference between the measured two response current values is a value larger than the pre-degraded state determination threshold value (step S202; YES), the control unit 33 determines that the state of the enzyme reagent layer of the sensor 4 is a pre-degraded state (step S204). Then, the control unit 33 performs, in step S204, processing similar to that of step S104. Specifically, in step S204, the control unit 33 stores, together with date and time of the determination, that the determination result of the state of the enzyme reagent layer is a pre-degraded state. When the external apparatus is not connected, the control unit 33 terminates the processing of step S204 and the second state detection processing.

Besides, when the external apparatus is connected, the control unit 33 transmits, to the external apparatus, information to inform the user that the enzyme reagent layer has been in a pre-degraded state. Thereafter, the control unit 33 terminates the processing of step S204 and the second state detection processing.

<<Third State Detection Processing>>

Figure 7:
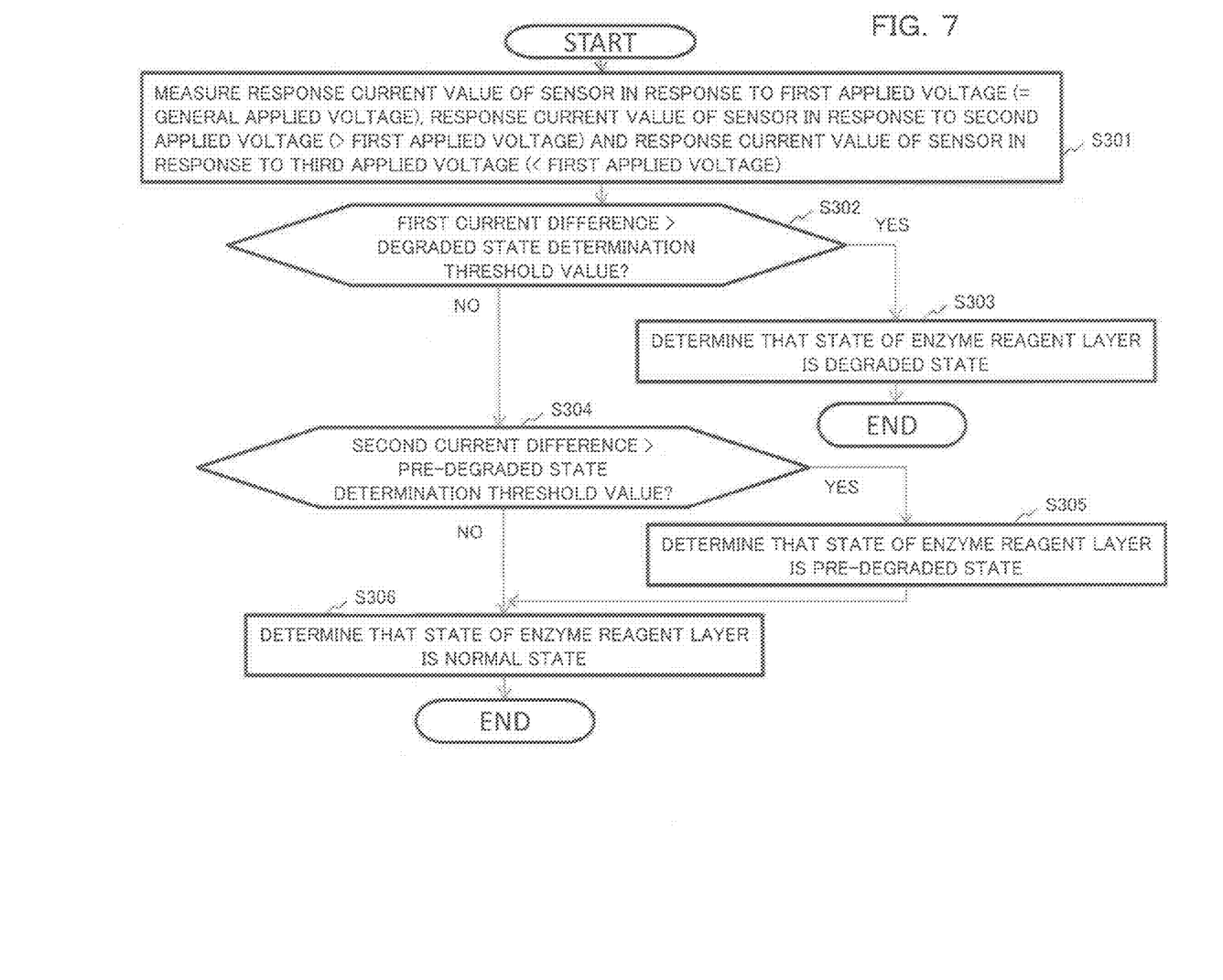
FIG. 7 is a flowchart of third state detection processing that may be executed by the control unit of the printed circuit.

The third state detection processing is processing performed through procedures illustrated in FIG. 7. Specifically, the control unit 33 having started the third state detection processing first controls the measuring unit 31 to measure a response current value of the sensor 4 in response to the first applied voltage, a response current value of the sensor 4 in response to the second applied voltage and a response current value of the sensor 4 in response to the third applied voltage (step S301).

Subsequently, the control unit 33 determines whether or not a first current difference corresponding to a difference between the two response current values measured under application of the second applied voltage and the first applied voltage is a value larger than the degraded state determination threshold value (step S301).

When the first current difference is a value larger than the degraded state determination threshold value (step S302; YES), the control unit 33 determines that the state of the enzyme reagent layer of the sensor 4 is a degraded state (step S303). In this step S303, the control unit 33 performs processing similar to that of step S103 described above. Then, the control unit 33 terminates the third state detection processing.

On the other hand, when the first current difference is a value equal to or smaller than the degraded state determination threshold value (step S302; NO), the control unit 33 determines whether or not a second current difference corresponding to a difference between the two response current values measured under application of the first applied voltage and the third applied voltage is a value larger than the pre-degraded state determination threshold value (step S304).

When the second current difference is a value larger than the pre-degraded state determination threshold value (step S304; YES), the control unit 33 performs, in step S305, processing similar to that of step S204 (FIG. 6). Alternatively, when the second current difference is a value equal to or smaller than the pre-degraded state determination threshold value (step S304; NO), the control unit 33 performs, in step S306, processing similar to that of steps S103 (FIG. 5) and S203 (FIG. 6).

Then, the control unit 33 having completed the processing of step S305 or S306 terminates the third state detection processing.

Now, the reason why a state of the enzyme reagent layer of the sensor 4 may be detected (determined) through the state detection processing having the above-described contents will be described.

Figure 8:
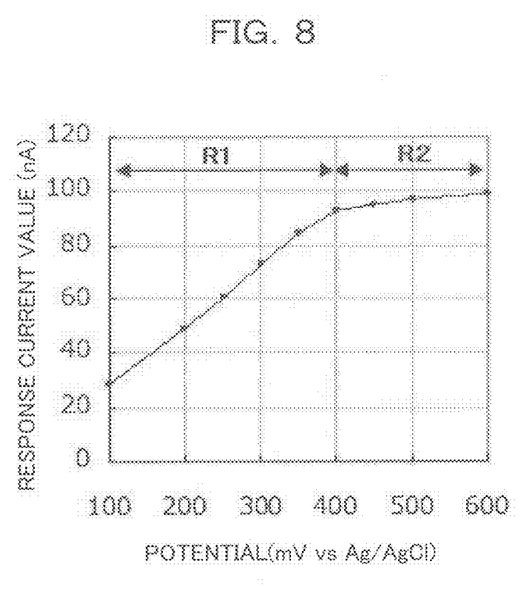
FIG. 8 is an explanatory diagram of an applied voltage/response current value characteristic of the sensor.
Figure 9:
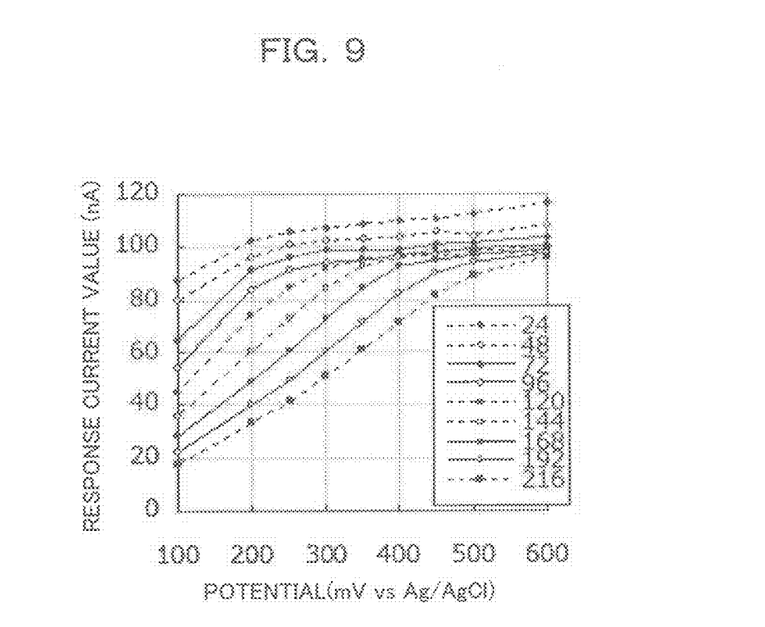
FIG. 9 is a graph illustrating results of the applied voltage/response current value characteristic of the sensor measured every 24 hours.

As a result of the earnest studies made by the present inventor, it was found that the applied voltage/response current value characteristics of the sensor 4 are as illustrated in FIG. 8 and FIG. 9. It is noted that FIG. 9 is a graph illustrating results of the applied voltage/response current value characteristics in a 600 mg/dL glucose solution, measured every 24 hours, of a sensor 4 including an Ag/AgCl electrode as the reference electrode. FIG. 8 is a graph illustrating merely the applied voltage/response current value characteristic attained when 168 hours have elapsed.

As illustrated in FIG. 8, as the applied voltage is increased, the response current value of the sensor 4 increases, in accordance with the increase in the applied voltage, at a substantially constant first increase rate up to a given applied voltage (of approximately 400 mV in FIG. 8). When the applied voltage is further increased, the response current value of the sensor 4 starts to increase, in accordance with the increase in the applied voltage, at a second increase rate smaller than the first increase rate (does not change much even if the applied voltage is increased). Incidentally, the sensor 4 exhibits such applied voltage/response current value characteristics because the sensor 4 is designed, for attaining a response in proportion to a substrate concentration, so that the diffusion of a substance through the outer layer film may be controlled rather than electron transfer from the enzyme to the electrode.

More specifically, as illustrated in FIG. 8, the sensor 4 has an applied voltage region R1 in which the response current value increases, in accordance with the increase in the applied voltage, at the substantially constant first increase rate, and an applied voltage region R2 in which the response current value increases, in accordance with the increase in the applied voltage, at the second increase rate much smaller than the first increase rate. Incidentally, although a boundary voltage between the applied voltage ranges R1 and R2 in the applied voltage/response current value characteristic illustrated in FIG. 8 is approximately 400 mV, the boundary voltage between the applied voltage ranges R1 and R2 may be a voltage not lower than 400 mV or a voltage not higher than 400 mV depending on the specific structure of the sensor 4.

The applied voltage dependence of the response current value of the sensor 4 is largely different between the applied voltage range R1 and the applied voltage range R2 because the enzyme reagent layer of the sensor 4 is covered with the outer layer film restricting the diffusion of the substrate. Specifically, since the enzyme reagent layer is covered with the outer layer film restricting the diffusion of the substrate, the sensor 4 may work in a charge-transfer controlled manner in some cases and in a diffusion controlled manner in the other cases. Here, to "work in a charge-transfer controlled manner" means to "be in a state where the response current value is determined in accordance with the rate of a charge transfer reaction from the enzyme to the electrode", and to "work in a diffusion controlled manner" means to "be in a state where the response current value is determined in accordance with a diffusion amount of the substrate through the outer layer film".

In working in a diffusion controlled manner, the response current value of the sensor 4 does not substantially depend on the applied voltage. Accordingly, when an applied voltage within the applied voltage range R2 is applied, the sensor 4 functions in a diffusion controlled state. On the other hand, in working in a charge-transfer controlled manner, the response current value of the sensor 4 varies depending on the applied voltage. Accordingly, the sensor 4 to which an applied voltage within the applied voltage range R1 is applied functions in a charge-transfer controlled state.

Besides, it was found, as illustrated in FIG. 9, that change over time of the response current value of the sensor 4 (a difference in the response current value between before and after a prescribed time period) is different depending on an applied voltage.

The procedures in the first through third state detection processing described above were conceived based on the above-described finding.

Figure 10:
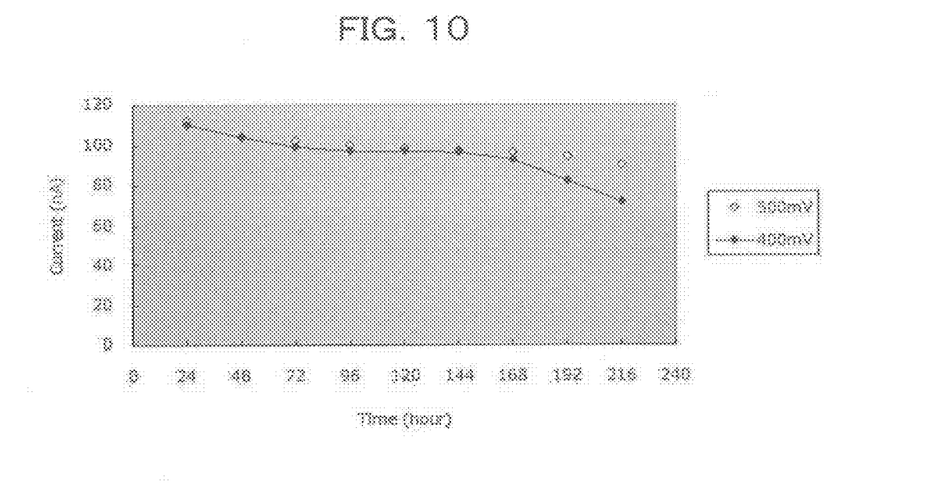
FIG. 10 is a graph illustrating change over time of a response current value obtained under application of a voltage of 400 mV and change over time of a response current value obtained under application of a voltage of 500 Mv.

Specifically, based on the experimental results illustrated in FIG. 9, a graph indicating the change over time of a response current value obtained under application of a voltage of 400 mV and the change over time of a response current value obtained under application of a voltage of 500 mV is created as illustrated in FIG. 10.

This graph reveals the following:

The response current value obtained under application of a voltage of 400 mV and the response current value obtained under application of a voltage of 500 mV are substantially the same value until 144 hours have elapsed after starting the measurement.

When 168 hours have elapsed at which the response current value obtained under application of a voltage of 400 mV starts to lower, the response current value obtained under application of a voltage of 500 mV starts to deviate from the response current value obtained under application of a voltage of 400 mV.

That the response current value obtained under application of a voltage of 400 mV and the response current value obtained under application of a voltage of 500 mV change as described above indicates that the diffusion controlled manner at the initial stage of the measurement changes to the charge-transfer controlled manner. Besides, since the charge transfer is affected by the reaction of the enzyme reagent layer, a phenomenon that the manner is changed to the charge-transfer manner (the response current value obtained under application of a voltage of 500 mV starts to deviate from the response current value obtained under application of a voltage of 400 mV) means that the enzyme reagent layer has been degraded.

In actual measurement of a glucose concentration by using the sensor 4, a glucose concentration to be measured is varied depending on a individual difference of a measurement target and a condition of the measurement target. Therefore, a response current value obtained under application of a voltage of 400 mV and a response current value obtained under application of a voltage of 500 mV do not change over time exactly as illustrated in FIG. 10. However, when the glucose concentration of the measurement target is different, the scale of the ordinate and/or the scale of the abscissa of the graph of FIG. 10 is merely varied. Accordingly, in the actual measurement of a glucose concentration by using the sensor 4, a response current value obtained under application of a voltage of 500 mV starts to deviate from a response current value obtained under application of a voltage of 400 mV on the date and time when the response current value obtained under application of a voltage of 400 mV starts to lower.

Besides, it may be determined, through the determination made in step S102 having the aforementioned contents, whether or not the phenomenon that a response current value of the sensor 4 in response to the second applied voltage (500 mV in the above description) deviates from a response current value of the sensor 4 in response to the first applied voltage (<the second applied voltage; 400 mV in the above description) has occurred. Therefore, the first state detection processing for detecting whether the state of the enzyme reagent layer is a degraded state or a normal state is performed as the processing having the above-described procedures.

Figure 11:
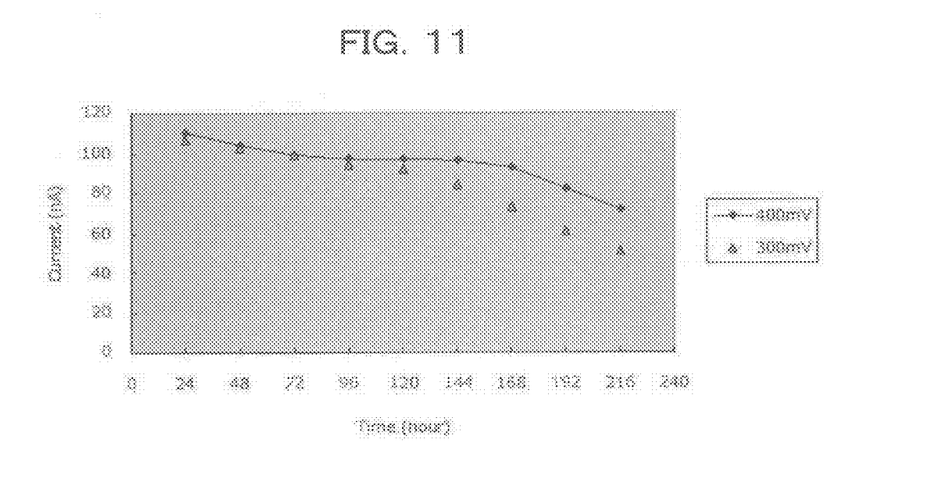
FIG. 11 is a graph illustrating change over time of a response current value obtained under application of a voltage of 400 mV and change over time of a response current value obtained under application of a voltage of 300 mV.

Besides, based on the experimental results illustrated in FIG. 9, a graph indicating the change over time of a response current value obtained under application of a voltage of 400 mV and the change over time of a response current value obtained under application of a voltage of 300 mV is created as illustrated in FIG. 11.

This graph reveals that the response current value obtained under application of a voltage of 300 mV starts to deviate from the response current value obtained under application of a voltage of 400 mV 48 hours before the response current value obtained under application of a voltage of 400 mV starts to lower. Besides, this phenomenon is derived also from the degradation of the enzyme reagent layer, and in actual measurement of a glucose concentration by using the sensor 4, the scale of the ordinate and/or the scale of the abscissa of the graph of FIG. 11 alone is varied. Accordingly, in the actual measurement of a glucose concentration by using the sensor 4, the response current value obtained under application of a voltage of 300 mV starts to deviate from the response current value obtained under application of a voltage of 400 mV on the date and time when the response current value obtained under application of 400 mV starts to lower (the date and time when the state of the enzyme reagent layer becomes a pre-degraded state).

Besides, it may be determined, through the determination made in step S202 having the aforementioned contents, whether or not the phenomenon that a response current value of the sensor 4 in response to the third applied voltage deviates from a response current value of the sensor 4 in response to the first applied voltage (>the third applied voltage) has occurred. Therefore, the second state detection processing for detecting whether the state of the enzyme reagent layer is a pre-degraded state or a normal state is performed as the processing having the above-described procedures.

Besides, in order that it may be detected whether the state of the enzyme reagent layer is a normal state, a pre-degraded state or a degraded state, processing corresponding to the first state detection processing and processing corresponding to the second state detection processing may be simultaneously performed. Therefore, the third state detection processing for detecting whether the state of the enzyme reagent layer is a normal state, a pre-degraded state or a degraded state is performed as the processing having the above-described procedures.

As described in detail so far, when the measuring apparatus 1 of the present embodiment is used, when the enzyme reagent layer of the sensor 4 has been in a pre-degraded state or a degraded state, a user may be informed of this via the external apparatus. Besides, when it is informed that the enzyme reagent layer has been in a pre-degraded state, the user may prepare a new sensor 4 well in advance. Furthermore, when it is informed that the enzyme reagent layer has been in a degraded state, the user may grasp that a measurement result obtained thereafter may be inaccurate in some cases, and may restore, by exchanging the sensor 4, the measuring apparatus 1 to a state where an accurate measurement result may be obtained. Accordingly, the measuring apparatus 1 of the present embodiment may be said as an apparatus difficult to disadvantage a user due to the degradation of the enzyme reagent layer of the sensor 4.

<<Modifications>>

The measuring apparatus 1 of the above-described embodiment may be variously modified. For example, the detection method for a state of the enzyme reagent layer performed by the measuring apparatus 1 may be applied to a sensor that is not of the subcutaneous indwelling type in which the diffusion is restricted without providing the outer layer film. Accordingly, the measuring apparatus 1 may be modified into an apparatus for such a sensor. Besides, the control unit 33 of the measuring apparatus 1 may be modified into a unit capable of executing fourth state detection processing performed through procedures illustrated in FIG. 12 instead of the first state detection processing or in addition to the first through third state detection processing.

Figure 12:
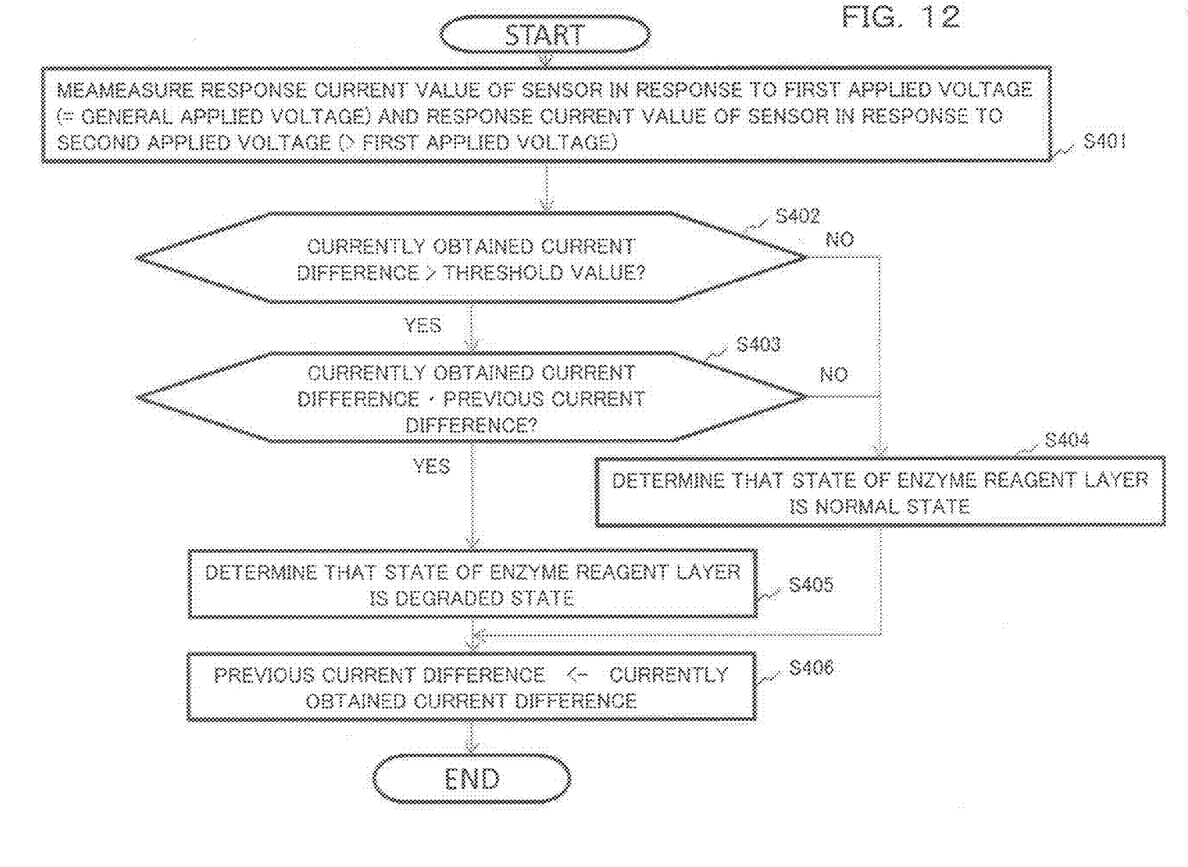
FIG. 12 is a flowchart of fourth state detection processing corresponding to a modification of the first state detection processing.

Processing in steps S401 and S402 of the fourth state detection processing is substantially the same as the processing of steps S101 and S102 of the first state detection processing. In the fourth state detection processing, however, when a currently obtained current difference corresponding to a difference between currently obtained two response current values exceeds a threshold value (step S402; YES), the currently obtained current difference is compared with a previous current difference corresponding to a difference between previously obtained two response current values (step S403). When the currently obtained current difference is larger than the previous current difference (step S403; YES), it is determined that the state of the enzyme reagent layer is a degraded state (step S405). Thereafter, processing for storing the currently obtained current difference as a previous current difference (step S406) is performed, and then the processing is terminated.

Incidentally, when the fourth state detection processing is branched to "NO" side as a result of the determination in step S403, it may be determined that the state of the enzyme reagent layer is a pre-degraded state. Besides, when the control unit 33 is constituted (programmed) to be capable of executing the fourth state detection processing, the resultant measuring apparatus 1 makes substantially no error determination that an enzyme reagent layer in a pre-degraded state or a normal state is in a degraded state.

It may be configured that a response current value of the sensor 4 in response to a fourth applied voltage higher than the second applied voltage is also measured in step S101 of the first state detection processing and that it is determined, in step S102, whether or not both a difference between two response current values of the sensor 4 in response to the fourth and second applied voltages and a difference between two response current values of the sensor 4 in response to the second and first applied voltages exceed a threshold value. Also the second state detection processing may be similarly modified.

Although the first applied voltage employed in the first through third state detection processing described above is the applied voltage employed in the general glucose concentration measurement, the first applied voltage may be a different applied voltage.

Besides, although the first through third state detection processing is performed separately from the general glucose concentration measurement processing (hereinafter referred to as the general measurement processing), each of the state detection processing may be modified into processing for detecting a state of an enzyme reagent layer by using a response current value measured for the general measurement processing. Besides, it goes without saying that the measuring apparatus 1 and the sensor 4 may be modified into an apparatus and a sensor for measuring a concentration of a substance different from glucose.

What is claimed is:

1. A measuring apparatus for measuring a substrate concentration by using a sensor containing an enzyme reagent layer, the measuring apparatus comprising:
a state detecting unit configured to apply a first voltage and a second voltage different from the first voltage to the sensor to detect a state of the enzyme reagent layer based on a difference between a first response current value obtained under application of the first voltage and a second response current value obtained under application of the second voltage,
wherein the state detecting unit is further configured to detect that the enzyme reagent layer is in a degraded state when the difference between the first and the second response current values is equal to or greater than a threshold value when the second voltage is of a higher voltage than the first voltage.

2. The measuring apparatus according to claim 1, wherein the sensor has a response current value that increases in accordance with an increase in an applied voltage substantially at a first increase rate when the applied voltage is in a low voltage range, and that increases at a second increase rate smaller than the first increase rate when the applied voltage is in a high voltage range higher than the low voltage range, and
at least one of the first voltage and the second voltage is a voltage within the high voltage range.

3. An electrochemical sensor connected to the measuring apparatus according to claim 1.

4. A measuring apparatus for measuring a substrate concentration by using a sensor containing an enzyme reagent layer, the measuring apparatus comprising:
a state detecting unit configured to apply a first voltage and a second voltage different from the first voltage to the sensor to detect a state of the enzyme reagent layer based on a difference between a first response current value obtained under application of the first voltage and a second response current value obtained under application of the second voltage,
wherein the state detecting unit is further configured to detect that the enzyme reagent layer is in a precursory state of a degraded state when the difference between the first and the second response current values is equal to or greater than a threshold value when the second voltage is of a lower voltage than the first voltage.

5. An electrochemical sensor connected to the measuring apparatus according to claim 4.

6. The measuring apparatus according to claim 4,
wherein the sensor has a response current value that increases in accordance with an increase in an applied voltage substantially at a first increase rate when the applied voltage is in a low voltage range, and that increases at a second increase rate smaller than the first increase rate when the applied voltage is in a high voltage range higher than the low voltage range, and
at least one of the first voltage and the second voltage is a voltage within the high voltage range.

7. A method for detecting a state of an enzyme reagent layer provided in a sensor, comprising:
applying a first voltage to the sensor to measure a response current value of the sensor in response to the first voltage;
applying a second voltage different from the first voltage to the sensor to measure a response current value of the sensor in response to the second voltage;
detecting the state of the enzyme reagent layer based on a difference between the measured two response current values; and
further detecting that the enzyme reagent layer is in a degraded state when the difference between the measured two response current values is equal to or greater than a threshold value when the second voltage is of a higher voltage than the first voltage.

8. The method according to claim 7,
wherein the sensor has a response current value that increases in accordance with an increase in an applied voltage substantially at a first increase rate when the applied voltage is in a low voltage range, and that increases at a second increase rate smaller than the first increase rate when the applied voltage is in a high voltage range higher than the low voltage range, and
at least one of the first voltage and the second voltage is a voltage within the high voltage range.

9. The method according to claim 7,
wherein the sensor is connected to a measuring apparatus.

10. A method for detecting a state of an enzyme reagent layer provided in a sensor, comprising:
applying a first voltage to the sensor to measure a response current value of the sensor in response to the first voltage;
applying a second voltage different from the first voltage to the sensor to measure a response current value of the sensor in response to the second voltage;
detecting the state of the enzyme reagent layer based on a difference between the measured two response current values; and
further detecting that the enzyme reagent layer is in a precursory state of a degraded state when the difference between the first and the second response current values is equal to or larger than a threshold value when the second voltage is of a lower voltage than the first voltage.

11. The method according to claim 10, wherein
the sensor has a response current value that increases in accordance with an increase in an applied voltage substantially at a first increase rate when the applied voltage is in a low voltage range, and that increases at a second increase rate smaller than the first increase rate when the applied voltage is in a high voltage range higher than the low voltage range, and at least one of the first voltage and the second voltage is a voltage within the high voltage range.

12. The method according to claim 10, wherein the sensor is connected to a measuring apparatus.

\* \* \* \* \*